United States Patent
Borate et al.

(10) Patent No.: US 9,181,269 B2
(45) Date of Patent: Nov. 10, 2015

(54) ENANTIOMERS OF FLUCONAZOLE ANALOGUES CONTAINING THIENO-[2,-3-D]PYRIMIDIN-4(3H)-ONE MOIETY AS ANTIFUNGAL AGENTS

(75) Inventors: Hanumant Bapurao Borate, Pune (IN); Suleman Riyajsaheb Maujan, Puna (IN); Sangmeshwer Prabhkara Sawargave, Pune (IN); Subhash Prataprao Chavan, Pune (IN); Mohan Anand Chandavarkar, Mumbai (IN); Ramkrishnan Ramachandran Iyer, Mumbai (IN); Vikas Vasant Nawathye, Mumbai (IN); Gajanan Jalindar Chavan, Mumbai (IN); Amit Chandrakant Tawte, Mumbai (IN); Deepali Damodar Rao, Mumbai (IN)

(73) Assignees: FDC Limited, Mumbai (IN); Council for Scientific & Industrial Research, New Delhi (IN)

( * ) Notice: Subject to any disclaimer, the term of this patent is extended or adjusted under 35 U.S.C. 154(b) by 92 days.

(21) Appl. No.: 14/004,869

(22) PCT Filed: May 31, 2011

(86) PCT No.: PCT/IN2011/000371
§ 371 (c)(1),
(2), (4) Date: Sep. 12, 2013

(87) PCT Pub. No.: WO2012/123952
PCT Pub. Date: Sep. 20, 2012

(65) Prior Publication Data
US 2014/0011818 A1    Jan. 9, 2014

(30) Foreign Application Priority Data
Mar. 15, 2011    (IN) .......................... 735/MUM/2011

(51) Int. Cl.
| | | |
|---|---|---|
| A01N 43/90 | (2006.01) | |
| A61K 31/519 | (2006.01) | |
| C07D 491/00 | (2006.01) | |
| C07D 495/00 | (2006.01) | |
| C07D 495/04 | (2006.01) | |

(52) U.S. Cl.
CPC ............ C07D 495/04 (2013.01); A61K 31/519 (2013.01)

(58) Field of Classification Search
None
See application file for complete search history.

(56) References Cited

U.S. PATENT DOCUMENTS 8,324,227 B2 * 12/2012 Borate et al. ................. 514/267

FOREIGN PATENT DOCUMENTS

| EP | 0472392 | 2/1992 | |
|---|---|---|---|
| EP | 1282084 | 2/2003 | |
| IN | WO2009109983 | * 9/2009 | ........... C07D 495/04 |
| WO | 9701552 | 1/1997 | |
| WO | 2009109983 | 9/2009 | |

OTHER PUBLICATIONS

Nguyen, et. al., International Journal of Biomedical Science, Jun. 2006; 2(2): 85-100.*
"International Search Report for PCTUS2011/000371 dated Sep. 26, 2011".
Aher, Nilkanth , "Synthesis and antifungal activity of 1,2,3-triazole containing fluconazole analogues", Bioorganic & Medicinal Chemistry Letters vol. 19, Issue 3, Feb. 1, 2009, pp. 759-763.
Giraud, Francis et al., "Synthesis and structure-activity relationships of 2-phenyl-1-[(pyridinyl-and piperidinylmethil)amino]-3(IH-1,2,4-tirazol-1-yl)propan-2ols as antifungal agents", Bioorganic & Medicinal Chemistry Letters vol. 19, Issue 2, Jan. 15, 2009, pp. 301-304.

(Continued)

*Primary Examiner* — Jeffrey H Murray
(74) *Attorney, Agent, or Firm* — Kramer Amado, P.C.

(57) ABSTRACT

The present invention discloses novel enantiomeric antifungal compounds of Formula (1a) and Formula (1b) containing thieno-[2,3-d]Jpyrimidin-4(3H)-one moiety and pharmaceutically acceptable salts thereof, method of preparing these compounds, the use of these compounds in prevention and treatment of fungal infections, and pharmaceutical preparations containing these compounds.

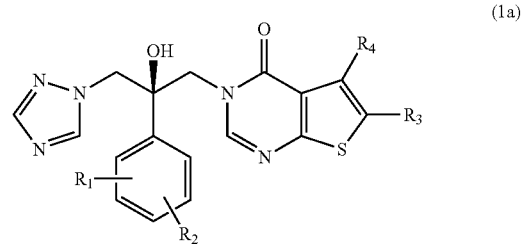

(1a)

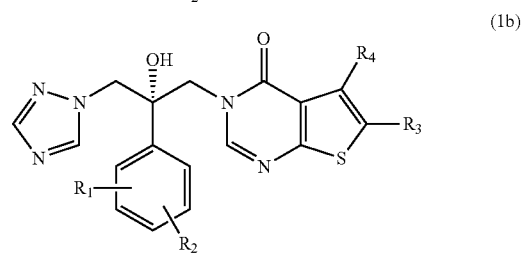

(1b)

20 Claims, No Drawings

(56) References Cited

OTHER PUBLICATIONS

Kagoshima, Yoshiko et al., "Synthesis, cleavage, and antifungal activity of a number of novel, water-soluble ester prodrugs of antifungal tirazole CS-758", Bioorganic & Medicinal Chemistry Letters vol. 19, Issue 13, Jul. 1, 2009, pp. 3559-3563.

Lebouvier, Nicolas et al., "Synthesis and antifungal activities of new fluconazole analogues with azaheterocyle moiety", Bioorganic & Medicinal Chemistry Letters vol. 17, Issue 13, Jul. 1, 2007, pp. 3686-3689.

Uchida, Takuya et al., "Amide analogs of antifungal dioxane-triazole derivatives: Syntehsis and in vitro activities", Bioorganic & Medicinal Chemistry Letters vol. 19, Issue 7, Apr. 1, 2009, pp. 2013-2017.

Uchida, Takuya et al., "Carbon analogs of antifungal dioxane-triazole derivatives: Synthesis and in vitro activities", Bioorganic & Medicinal Chemistry Letters vol. 18, Issue 24, Dec. 15, 2008, pp. 6538-6541.

\* cited by examiner

ENANTIOMERS OF FLUCONAZOLE ANALOGUES CONTAINING THIENO-[2,-3-D]PYRIMIDIN-4(3H)-ONE MOIETY AS ANTIFUNGAL AGENTS

FIELD OF INVENTION

The present invention relates to enantiomers of fluconazole analogues containing thieno-[2,3-d]pyrimidin-4(3H)-one moiety as antifungal agents, which are depicted by Formula (1a) and Formula (1b), and pharmaceutically acceptable salts thereof, Formula (1a)

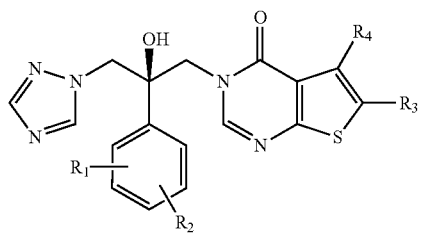

Formula (1b)

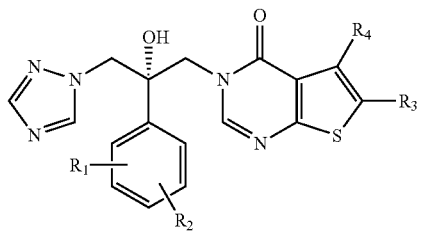

Wherein $R_1$ is hydrogen or a halogen selected from fluorine, chlorine, bromine or iodine; $R_2$ is hydrogen or a halogen selected from fluorine, chlorine, bromine or iodine; and $R_3$ and $R_4$ may be the same or different, and each represents a hydrogen, alkyl group of linear or branched chain of 1 to 20 carbon atoms optionally substituted with aryl group, hydroxyl group, alkanoate group, acetoxy group, amino acetoxy group, N-Boc-amino acetoxy group, alkoxy (—OR) group (wherein R=alkyl group with 1 to 4 carbon atoms), benzyloxy, arylalkyl group (wherein the aryl group is phenyl optionally substituted with alkyl group of 1 to 3 carbon atoms); or $R_3$ and $R_4$ together form a cycloalkyl ring of 3 to 10 carbon atoms.

The invention further relates to a process for preparation of the enantiomers of fluconazole analogues containing thieno-[2,3-d]pyrimidin-4(3H)-one moiety of Formula (1a) and Formula (1b), and pharmaceutical preparations containing these compounds for prevention and treatment of fungal infections.

BACKGROUND OF THE INVENTION

Fungus is a type of microorganism that causes fungal infection. A fungal infection is an inflammatory condition in which fungi multiply and invade the skin, the digestive tract, the genitals and other body tissues, particularly the lungs and liver. Fungal infections mainly include superficial and systemic fungal infections. Fungal infections are more common in people taking antibiotics, corticosteroids, immunosuppressant drugs and contraceptives. The fungal infections are prominent in people with endocrine disorders, immune diseases and other conditions such as obesity, AIDS, tuberculosis, major burns, leukemia and diabetes.

The current antifungal agents belong to various groups like polyenes, heterocyclic benzofuran, allylamines, antimetabolites, azoles, glucan synthesis inhibitors, etc. out of which azoles are presently the most extensively used antifungal agents. Azoles are further classified into imidazoles and triazoles. Fluconazole belongs to the family of triazole antifungals. Fluconazole is an important antifungal agent which is orally active and has low toxicity but its extensive use has resulted in emergence of fluconazole-resistant fungal strains. Therefore, it is necessary to meet the long-felt need to develop novel fluconazole analogues which exert high anti-fungal activity against various fungi. The presence of one triazole ring, halogenated phenyl ring and tertiary alcoholic oxygen functionality in azole class of compounds, is necessary for antifungal activity.

Various fluconazole analogues having antifungal activity have been reported in the literature. Some of the recent references describing synthesis and antifungal activity are given below:

Bioorganic & Medicinal Chemistry Letters 17 (2007) 3686-9; Bioorganic & Medicinal Chemistry Letters 18 (2008) 6538-6541; Bioorganic & Medicinal Chemistry Letters 19 (2009) 301-304; Bioorganic & Medicinal Chemistry Letters 19 (2009) 759-763; Bioorganic & Medicinal Chemistry Letters 19 (2009) 2013-2017; and Bioorganic & Medicinal Chemistry Letters 19 (2009) 3559-3563.

The racemic fluconazole analogues containing thieno-[2,3-d]pyrimidin-4(3H)-one moiety of Formula (2) and their excellent antifungal activities have already been described in our earlier patent publication, WO 2009109983, with the method of preparing such racemic compounds, which have high antifungal activity against various fungi.

Formula (2)

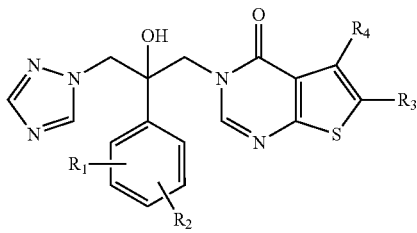

Wherein, $R_1$, $R_2$, $R_3$ and $R_4$ are defined as above.

It has been found by the present inventors that one of the enantiomer of chiral fluconazole analogues containing thieno-[2,3-d]pyrimidin-4(3H)-one moiety has enhanced antifungal activity than corresponding racemic compounds. Hence, there is a need to develop such enantiomers which exert high antifungal activity against various fungal strains.

Accordingly, the present invention seeks to provide enantiomers of chiral fluconazole analogues of Formula (1a) and Formula (1b) containing thieno-[2,3-d]pyrimidin-4(3H)-one moiety and process thereof as an effort to come up with antifungal agents having broad spectrum of antifungal activity, for which the protection is sought.

OBJECT OF THE INVENTION

The primary objective of the present invention is to provide compounds of Formula (1a) and Formula (1b) containing thieno-[2,3-d]pyrimidin-4(3H)-one moieties with enhanced antifungal activity against various fungal strains.

Another objective of the present invention is to provide a process for the preparation of compounds of Formula (1a) and Formula (1b) containing thieno-[2,3-d]pyrimidin-4(3H)-one moieties having enhanced antifugal activity.

SUMMARY OF THE INVENTION

Accordingly, to meet the above stated objectives, the present invention discloses enantiomers of fluconazole analogues containing thieno-[2,3-d]pyrimidin-4(3H)-one moiety as antifungal agents, which are depicted by Formula (1a) and Formula (1b).

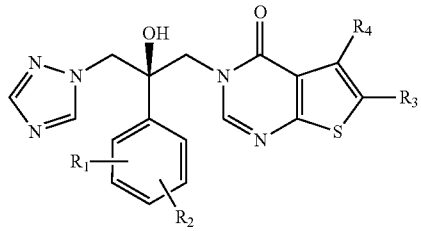

Formula (1a)

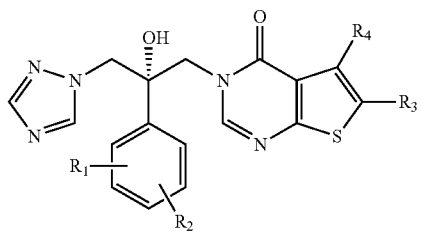

Formula (1b)

Wherein $R_1$ is hydrogen or a halogen selected from fluorine, chlorine, bromine or iodine; $R_2$ is hydrogen or a halogen selected from fluorine, chlorine, bromine or iodine; and $R_3$ and $R_4$ may be the same or different, and each represents a hydrogen, alkyl group of linear or branched chain of 1 to 20 carbon atoms optionally substituted with aryl group, hydroxyl group, alkanoate group, acetoxy group, amino acetoxy group, N-Boc-amino acetoxy group, alkoxy (—OR) group (wherein R=alkyl group with 1 to 4 carbon atoms), benzyloxy, arylalkyl group (wherein the aryl group is phenyl optionally substituted with alkyl group of 1 to 3 carbon atoms; or $R_3$ and $R_4$ together form a cycloalkyl ring of 3 to 10 carbon atoms. The invention encompasses the pharmaceutical salts of Formula (1a) and (1b).

The invention further discloses a process for preparation of compounds of Formula (1a) and Formula (1b), and pharmaceutical preparations containing these compounds, for prevention and treatment of fungal infections. Such chiral, optically-active compounds acting as antifungals, have MIC values much smaller than that of racemic compounds of Formula (2) as well as fluconazole.

DETAILED DESCRIPTION

According to the present invention, there are provided pure enantiomers of fluconazole analogues containing thieno-[2,3-d]pyrimidin-4(3H)-one moiety, as depicted in Formula (1a) and Formula (1b). These compounds belong to azole class of antifungal compounds and are analogues of fluconazole, which is active against fungi; and are to be used in pharmaceutical preparations as active agent.

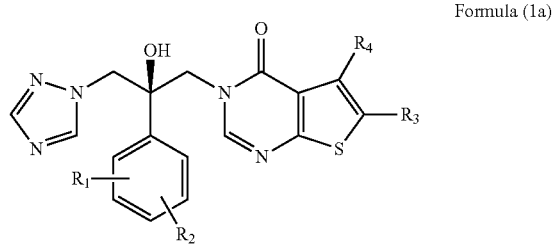

Formula (1a)

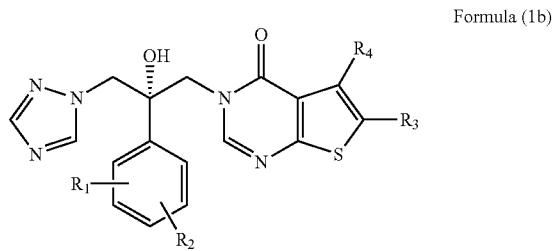

Formula (1b)

Wherein $R_1$ is hydrogen or a halogen selected from fluorine, chlorine, bromine or iodine; $R_2$ is hydrogen or a halogen selected from fluorine, chlorine, bromine or iodine; and $R_3$ and $R_4$ may be the same or different, and each represents a hydrogen, alkyl group of linear or branched chain of 1 to 20 carbon atoms optionally substituted with aryl group, hydroxyl group, alkanoate group, acetoxy group, amino acetoxy group, N-Boc-amino acetoxy group, alkoxy (—OR) group (wherein R=alkyl group with 1 to 4 carbon atoms), benzyloxy, arylalkyl group (wherein the aryl group is phenyl optionally substituted with alkyl group of 1 to 3 carbon atoms); or $R_3$ and $R_4$ together form a cycloalkyl ring of 3 to 10 carbon atoms.

The invention further relates to the process for preparation of the compounds of Formula (1a) and Formula (1b). The compounds of Formula (1a) and Formula (1b) of the present invention are prepared either by a synthetic process as illustrated in Scheme 1, or by chiral separation using HPLC (High Performance Liquid Chromatography) as illustrated in Scheme 2.

Scheme 1:

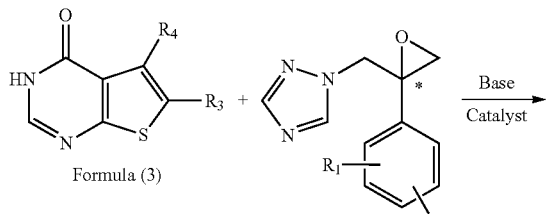

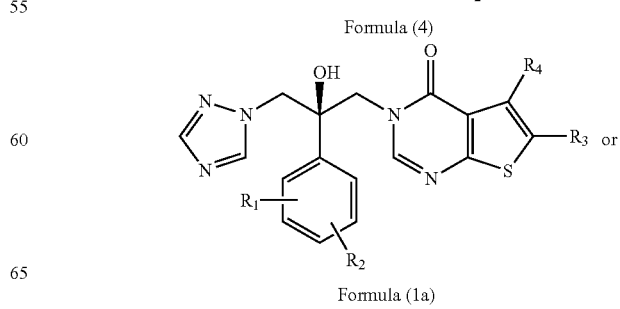

Formula (1a)

-continued

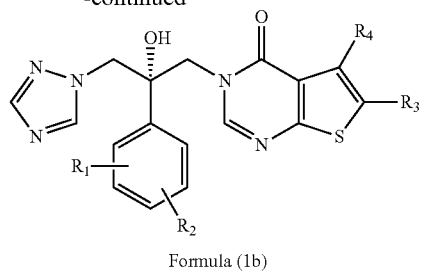

Formula (1b)

Wherein, $R_1$, $R_2$, $R_3$ and $R_4$ are defined as above, and "*" is used to designate R or S configuration at carbon atom.

Accordingly, the process for the preparation of compound of Formula (1a) and Formula (1b) comprises reacting a compound of Formula (3) with a chiral epoxide of Formula (4), in presence of a suitable base and a catalyst. The suitable base used in the present invention is selected from various organic or inorganic bases preferably inorganic base such as potassium carbonate, sodium carbonate or cesium carbonate. The suitable catalyst used in the present invention is selected from various phase transfer catalysts such as tetrabutylammonium bromide, trtrabutylammonium chloride, triethylbenzylammonium chloride or cetyltrimethylammonium bromide.

Scheme 2:

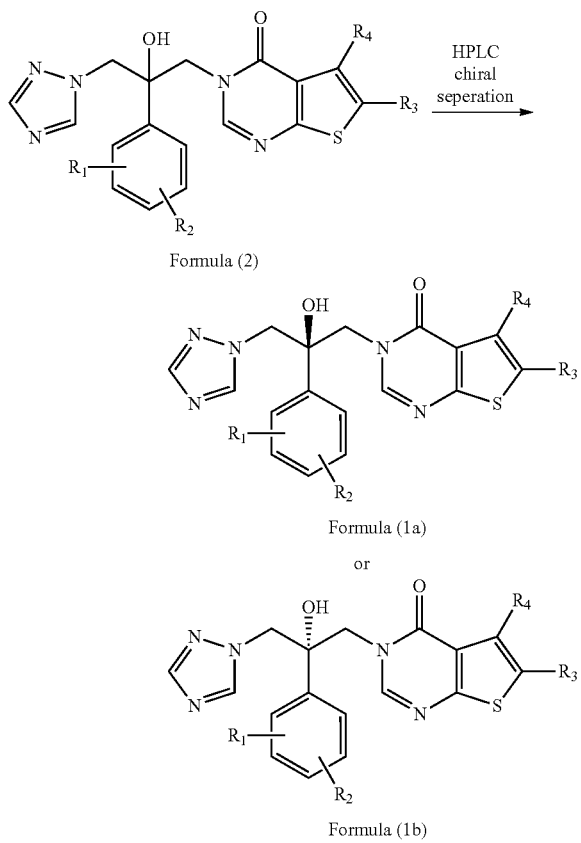

Wherein, $R_1$, $R_2$, $R_3$ and $R_4$ are defined as above.

Compounds of Formula (1a) and Formula (1b) can also be prepared by chiral separation of racemic compounds of Formula (2) using chiral HPLC in order to obtain desired enantiomer, as shown in Scheme 2. The chiral HPLC is performed using a chiral preparative HPLC column and a mobile phase. Compounds of Formula (2) can be prepared as per the method disclosed in WO 2009109983.

According to the present invention, the chiral preparative HPLC column is selected from but not limited to cellulose tris (3,5-dimethylphenylcarbamate) coated on silica-gel, cellulose tris (4-methylbenzoate) coated on silica-gel or tris-(3,5-dimethylphenyl)-carbamoyl amylose coated on silica-gel; and the eluent system is isocratic system comprising a mixture of hydrocarbon(s), alcohol(s) and/or alkylamine(s).

The hydrocarbons used in the present invention are selected from a group consisting of pentane, hexane, heptane, iso-octane, cyclohexane and cyclopentane.

The alcohol used in the present invention is selected from the group consisting of methanol, ethanol, propan-1-ol, propan-2-ol, butan-1-ol, butan-2-ol, tert-butanol, 3-methyl-1-butanol, 2-methyl-1-propanol, 2-methoxyethanol and 2-ethoxyethanol.

The alkylamine used in the present invention is selected from a group consisting of diethylamine, triethylamine, iso-propylamine and butylamine.

The ratio of alcohol in the mobile phase of the eluent system ranges from 10% to 60%. The ratio of hydrocarbon in the mobile phase of the eluent system ranges from 40% to 90%. The ratio of alkylamine in the mobile phase of the eluent system ranges from 0% to 2%.

The present invention further discloses a pharmaceutical preparation for treating or preventing fungal infections, comprising compounds of Formula (1a) or Formula (1b), in association with at least one pharmaceutically acceptable excipient known in the art. These excipients are added to the composition for variety of purposes.

The pharmaceutical preparations according to the invention may be administered as oral, topical and parenteral dosage forms.

The pharmaceutical preparations can be selected from various oral dosage forms such as solid dosage form including tablets, capsules, pellets, powders, soft gelatin capsules and oral liquids. The pharmaceutical compositions can be prepared using conventional techniques well known in the art.

The invention provides a method for treating or preventing fungal infections in a subject, wherein the said method comprises administering to the subject, therapeutically effective amounts of the compounds of Formula (1a) or Formula (1b) of the present invention. The subject according to the invention is a mammal. The compounds of the present invention can also be administered optionally with other actives depending on the disease conditions.

The term "therapeutically effective amount" as used herein, means an amount used in the pharmaceutical preparations to achieve the desired therapeutic effect.

The amount/quantity of the compound used in pharmaceutical compositions of the present invention will vary depending upon the body weight of the patient, and the mode of administration and can be of any effective amount to achieve the desired therapeutic effect.

The present invention further provides use of the compound of Formula (1a) or (1b) in the treatment and prevention of variety of fungal diseases. The active compounds of Formula (1a) or (1b) are effective against variety of fungal species.

The present invention also provides the use of compound of Formula (1a) or (1b) in the preparation of pharmaceutical medicament for the treatment and prevention of variety of fungal diseases.

The pharmaceutical medicament according to the invention may be administered as oral, topical and parenteral dosage forms.

The invention is further illustrated with the following examples and should not be construed to limit the scope of the present invention. The features of the present invention will become more apparent from the following description of the inventive concept and the description of the preferred embodiments.

Some of the compounds of Formula 1a, 1b, 2, 3 and 4 are illustrated in Tables 1,2,3,4 and 5 respectively.

Compounds of Formula (1a):

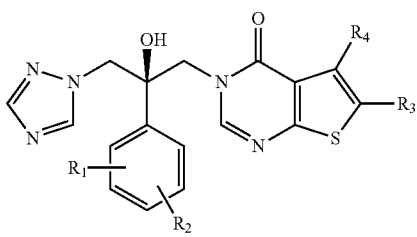

TABLE 1

| Compd No. | $R_1$ | $R_2$ | $R_3$ | $R_4$ | Structure |
|---|---|---|---|---|---|
| 1a-01 | 2-F | 4-F | n-hexyl | H | 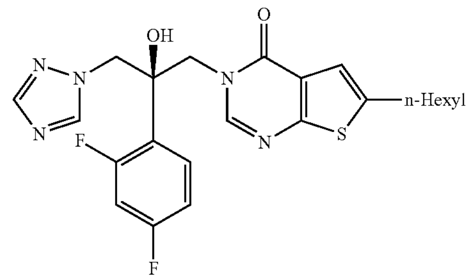 |
| 1a-02 | 2-F | 4-F | n-pentyl | H | 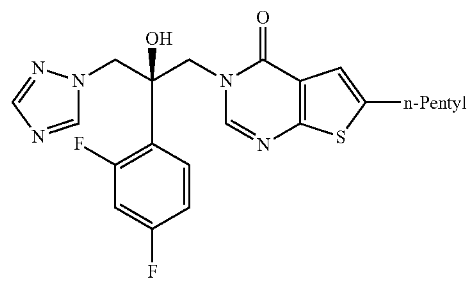 |
| 1a-03 | 2-F | 4-F | n-heptyl | H | 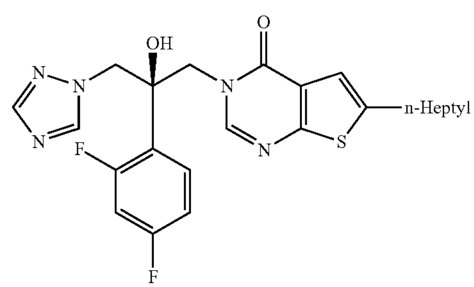 |
| 1a-04 | 2-F | 4-F | n-propyl | H | 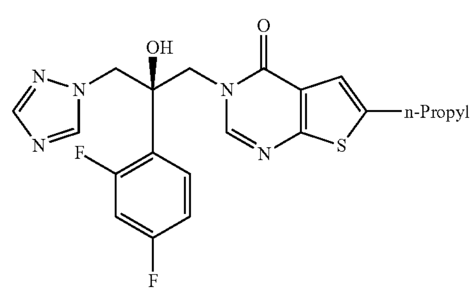 |

Compounds of Formula (1b):
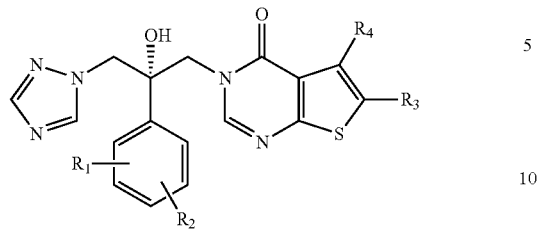
TABLE 2
| Compd No. | R₁ | R₂ | R₃ | R₄ | Structure |
|---|---|---|---|---|---|
| 1b-01 | 2-F | 4-F | n-hexyl | H | 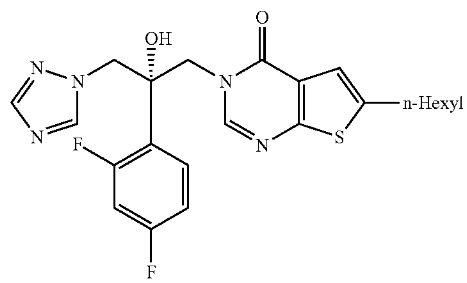 |
| 1b-02 | 2-F | 4-F | n-pentyl | H | 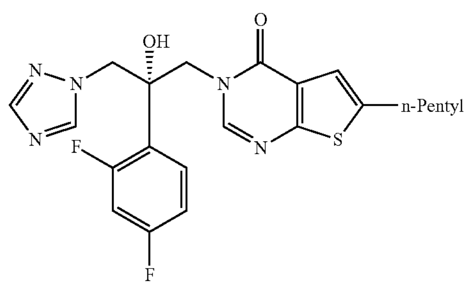 |
| 1b-03 | 2-F | 4-F | n-heptyl | H | 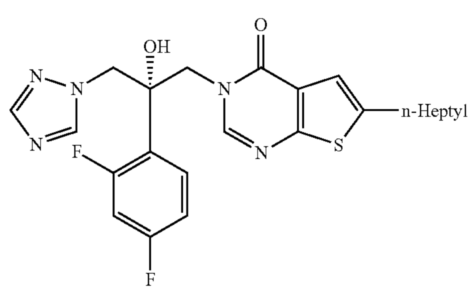 |
| 1b-04 | 2-F | 4-F | n-propyl | H | 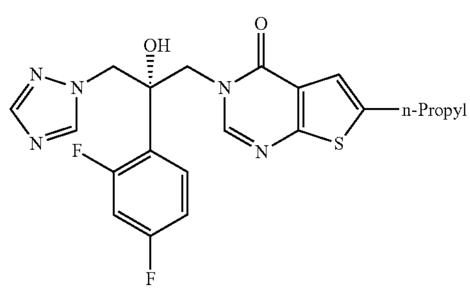 |

Compounds of Formula (2):
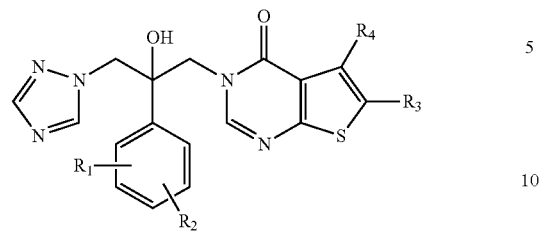
TABLE 3
| Compd No. | R$_1$ | R$_2$ | R$_3$ | R$_4$ | Structure |
|---|---|---|---|---|---|
| 2-01 | 2-F | 4-F | n-hexyl | H | 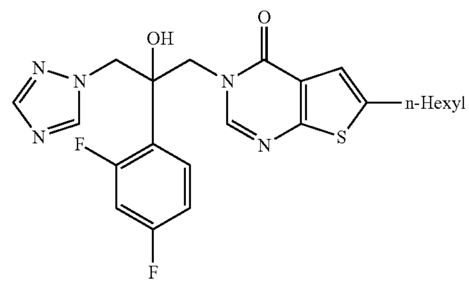 |
| 2-02 | 2-F | 4-F | n-pentyl | H | 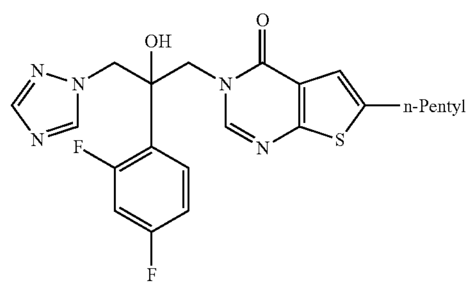 |
| 2-03 | 2-F | 4-F | n-heptyl | H | 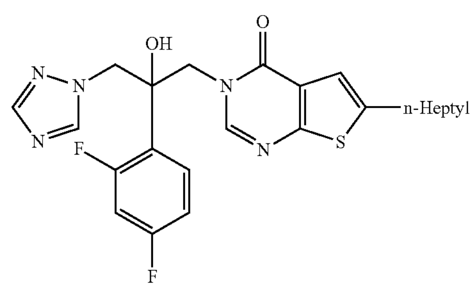 |
| 2-04 | 2-F | 4-F | n-propyl | H | 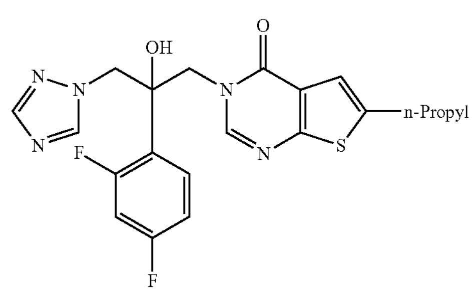 |

Compounds of Formula (3):

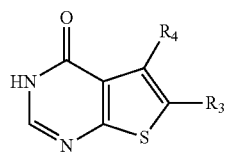

TABLE 4

| Compd No. | R$_3$ | R$_4$ | Structure |
|---|---|---|---|
| 3-01 | n-hexyl | H | (n-Hexyl structure) |
| 3-02 | n-pentyl | H | (n-Pentyl structure) |
| 3-03 | n-heptyl | H | (n-Heptyl structure) |
| 3-04 | n-propyl | H | (n-Propyl structure) |

Compounds of Formula (4)

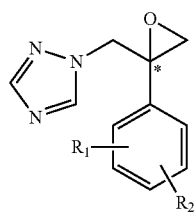

TABLE 5

| Compd No. | R$_1$ | R$_2$ | Structure |
|---|---|---|---|
| 4a | 2-F | 4-F | (structure) |
| 4b | 2-F | 4-F | (structure) |

EXAMPLES

General Method of Preparation of Compounds of Formula (1a) and Formula (1b) Via Scheme 1

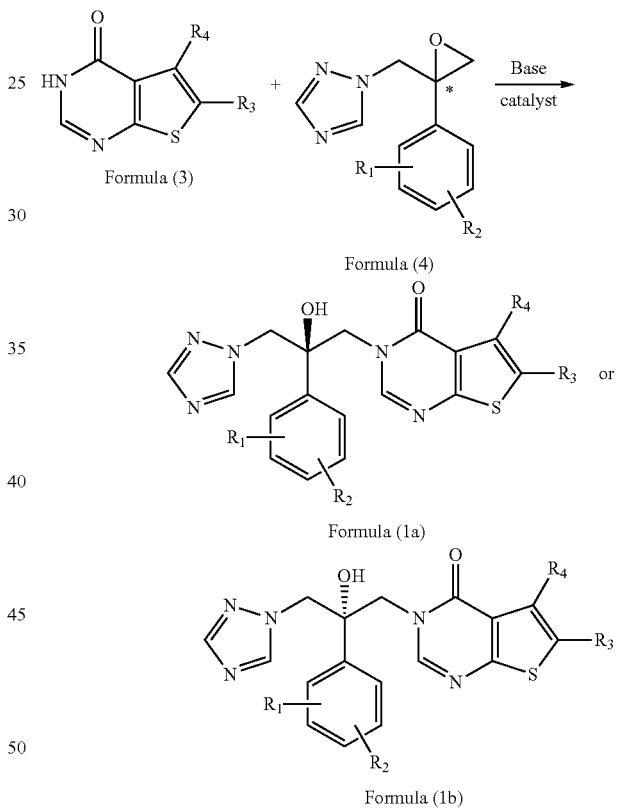

Wherein, R$_1$, R$_2$, R$_3$ and R$_4$ are defined as above, and "*" is used to designate R or S configuration at carbon atom.

Compound of Formula 3 (1 equivalent) was taken in two necked round bottom flask equipped with reflux condenser and guard tube. Organic solvent such as ethyl acetate was added followed by the addition of flame-dried base (0.5-4 equivalents) and catalyst (0.1-2 equivalent). The mixture was stirred at room temperature for 0.5-4 h and compound of Formula 4a (1 equivalent) in ethyl acetate was added. The mixture was stirred under reflux for 5-18 h, cooled, diluted with water, extracted with ethyl acetate, dried over Na$_2$SO$_4$ and concentrated. Purification by recrystallization from ethyl acetate afforded the pure product.

Example 1

(S)-3-[2-(2,4-Difluorophenyl)-2-hydroxy-3-[1,2,4]triazol-1-yl-propyl]-6-(n-hexyl)-thieno[2,3-d]pyrimidin-4(3H)-one (Formula 1b-01)

6-(n-Hexyl)thieno[2,3-d]pyrimidin-4(3H)-one (Formula 3-01) (0.99 g, 4.21 mmol) was taken in two necked round bottom flask equipped with reflux condenser and guard tube. Ethyl acetate (50 ml) was added followed by the addition of flame dried potassium carbonate (1.16 g, 8.43 mmol) and tetrabutylammonium bromide (1.36 g, 4.21 mmol). The mixture was stirred at room temperature for 1 h and (R)-1-[2-(2,4-difluorophenyl)-oxiranylmethyl]-1H-[1,2,4]triazole (Formula 4b) (1.0 g, 4.21 mmol) in ethyl acetate (20 ml) was added. The mixture was stirred under reflux for 12 h, cooled, diluted with water (100 ml), extracted with ethyl acetate (3×40 ml), dried over $Na_2SO_4$ and concentrated. Purification on column chromatography afforded the pure product as pale brown solid (1.51 g, 75.7%).

Nature: Pale brown solid; MP: 90° C.; Yield: 75.7%; $^1$H NMR (200 MHz, $CDCl_3$): δ 0.88 (t, J=6 Hz, 3H), 1.21-1.48 (m, 6H), 1.61-1.76 (m, 2H), 2.82 (t, J=8 Hz, 2H), 4.22 (d, J=14 Hz, 1H), 4.52 (d, J=14 Hz, 1H), 4.72 (d, J=14 Hz, 1H), 4.80 (d, J=14 Hz, 1H), 6.24 (s, 1H), 6.75-6.89 (m, 2H), 7.07 (s, 1H), 7.48-7.62 (m, 1H), 7.83 (s, 1H), 7.91 (s, 1H), 8.10 (s, 1H); $[α]_D^{25}$=+96° (c=1.0, Chloroform).

Example 2

Preparation of (S)-3-[2-(2,4-difluorophenyl)-2-hydroxy-3-(1H-1,2,4-triazol-1-yl)propyl]-6-n-pentylthieno[2,3-d]pyrimidin-4(3H)-one (Formula 1b-02)

6-(n-Pentyl)thieno[2,3-d]pyrimidin-4(3H)-one (Formula 3-02) (4.6 g, 0.021 mol) was taken in two necked round bottom flask equipped with reflux condenser and guard tube. Ethyl acetate (250 ml) was added followed by the addition of flame dried potassium carbonate (5.72 g, 0.042 mol) and tetrabutylammonium bromide (6.693 g, 0.021 mol). The mixture was stirred at room temperature for 30 min and (R)-1-[2-(2,4-difluorophenyl)-oxiranylmethyl]-1H-[1,2,4]triazole (Formula 4b) (4.91 g, 0.021 mol) in ethyl acetate (50 ml) was added. The mixture was stirred under reflux for 14 h, cooled, diluted with water (250 ml), extracted with ethyl acetate (3×150 ml), dried over $Na_2SO_4$ and concentrated. Purification by recrystallization from ethyl acetate afforded the pure product as pale yellow solid (7.11 g, 73.8%).

Nature: Pale yellow solid; MP: 152° C.; Yield: 73.8%; $^1$H NMR (200 MHz, $CDCl_3$): δ 0.90 (t, J=6 Hz, 3H), 1.27-1.42 (m, 4H), 1.64-1.76 (m, 2H), 2.82 (t, J=8 Hz, 2H), 4.21 (d, J=15 Hz, 1H), 4.52 (d, J=15 Hz, 1H), 4.71 (d, J=15 Hz, 1H), 4.78 (d, J=15 Hz, 1H), 6.24 (s, 1H), 6.76-6.88 (On, 2H), 7.06 (s, 1H), 7.50-7.64 (m, 1H), 7.81 (s, 1H), 7.90 (s, 1H), 8.09 (s, 1H); $[α]_D^{25}$=+98° (c=1.0, Chloroform).

Example 3

(S)-3-[2-(2,4-Difluorophenyl)-2-hydroxy-3-[1,2,4]triazol-1-yl-propyl]-6-n-heptyl-thieno[2,3-d]pyrimidin-4(3H)-one (Formula 1b-03)

6-(n-Heptyl)thieno[2,3-d]pyrimidin-4(3H)-one (Formula 3-03) (0.502 g, 0.0021 mol) was taken in two necked round bottom flask equipped with reflux condenser and guard tube. Ethyl acetate (10 nil) was added followed by the addition of flame dried potassium carbonate (0.582 g, 0.0042 mol) and tetrabutylammonium bromide (0.681 g, 0.0021 mol). The mixture was stirred at room temperature for 1 h and (R)-1-[2-(2,4-difluorophenyl)-oxiranylmethyl]-1H-[1,2,4]triazole (Formula 4b) (0.50 g, 0.0021 mol) in ethyl acetate (5 ml) was added. The mixture was stirred under reflux for 12 h, cooled, diluted with water (50 ml), extracted with ethyl acetate (3×20 ml), dried over $Na_2SO_4$ and concentrated. Purification by column chromatography afforded the pure product as cream white solid (0.834 g, 81.2%).

Nature: Cream white solid; MP: 98° C.; Yield: 81.2%; $^1$H NMR (200 MHz, $CDCl_3$): δ 0.86 (t, J=6 Hz, 3H), 1.21-1.32 (m, 8H), 1.62-1.72 (m, 2H), 2.81 (t, J=8 Hz, 2H), 4.23 (d, J=15 Hz, 1H), 4.53 (d, J=15 Hz, 1H), 4.72 (d, J=15 Hz, 1H), 4.80 (d, J=15 Hz, 1H), 6.24 (bs, 1H), 6.74-6.89 (m, 2H), 7.06 (s, 1H), 7.48-7.60 (m, 1H), 7.84 (s, 114), 7.91 (s, 1H), 8.13 (s, 1H); $[α]_D^{25}$=+110° (c=1.0, Chloroform).

Example 4

(S)-3-[2-(2,4-Difluorophenyl)-2-hydroxy-3-[1,2,4]triazol-1-yl-propyl]-6-(n-propyl)-thieno[2,3-d]pyrimidin-4(3H)-one (Formula 1b-04)

6-(n-Propyl)thieno[2,3-d]pyrimidin-4(3H)-one (Formula 3-04) (0.82 g, 0.0042 mol) was taken in two necked round bottom flask equipped with reflux condenser and guard tube. Ethyl acetate (15 ml) was added followed by the addition of flame dried potassium carbonate (1.16 g, 0.0084 mol) and tetrabutylammonium bromide (1.36 g, 0.0042 mol). The mixture was stirred at room temperature for 0.5 h and (R)-1-[2-(2,4-difluorophenyl)-oxiranylmethyl]-1H-[1,2,4]triazole (Formula 4b) (1.00 g, 0.0042 mol) in ethyl acetate (10 ml) was added. The mixture was stirred under reflux for 12 h, cooled, diluted with water (50 ml), extracted with ethyl acetate (4×25 ml), dried over $Na_2SO_4$ and concentrated. Purification on column chromatography afforded the pure product as off-white solid (1.36 g, 74.6%).

Nature: Off-white solid; MP: 94° C.; Yield: 74.6%; $^1$H NMR (200 MHz, $CDCl_3$): δ 0.99 (t, J=7 Hz, 3H), 1.61-1.83 (m, 2H), 2.80 (t, J=8 Hz, 2H), 4.27 (d, J=14 Hz, 1H), 4.59 (d, J=14 Hz, 1H), 4.73 (d, J=14 Hz, 1H), 4.84 (d, J=14 Hz, 1H), 6.28 (bs, 1H), 6.74-6.90 (m, 2H), 7.08 (s, 1H), 7.46-7.61 (m, 1H), 7.88 (s, 1H), 7.92 (s, 1H), 8.28 (s, 1H); $[α]_D^{25}$=+92° (c=1.0, Chloroform).

Example 5

Preparation of (R)-3-[2-(2,4-difluorophenyl)-2-hydroxy-3-(1H-1,2,4-triazol-1-yl)propyl]-6-n-pentylthieno[2,3-d]pyrimidin-4(3H)-one (Formula 1a-02)

6-(n-Pentyl)thieno[2,3-d]pyrimidin-4(3H)-one (Formula 3-02) (1.00 g, 4.21 mmol) was taken in two necked round bottom flask equipped with reflux condenser and guard tube. Ethyl acetate (30 ml) was added followed by the addition of flame dried potassium carbonate (1.16 g, 8.43 mmol) and tetrabutylammonium bromide (1.36 g, 4.21 mmol). The mixture was stirred at room temperature for 1 h and (S)-1-[2-(2,4-difluorophenyl)-oxiranylmethyl]-1H-[1,2,4]triazole (Formula 4a) (1.0 g, 4.21 mmol) in ethyl acetate (50 ml) was added. The mixture was stirred under reflux for 12 h, cooled, diluted with water (100 ml), extracted with ethyl acetate (3×40 ml), dried over $Na_2SO_4$ and concentrated. Purification by recrystallization from ethyl acetate afforded the pure product as pale yellow solid (1.44 g, 74.6%).

Nature: Pale yellow solid; MP: 153° C.; Yield: 73.8%; $^1$H NMR (200 MHz, $CDCl_3$): δ 0.90 (t, J=6 Hz, 3H), 1.27-1.42

(m, 4H), 1.64-1.76 (m, 2H), 2.82 (t, J=8 Hz, 2H), 4.21 (d, J=15 Hz, 1H), 4.52 (d, J=15 Hz, 1H), 4.71 (d, J=15 Hz, 1H), 4.78 (d, J=15 Hz, 1H), 6.24 (s, 1H), 6.76-6.88 (m, 2H), 7.06 (s, 1H), 7.50-7.64 (m, 1H), 7.81 (s, 1H), 7.90 (s, 1H), 8.09 (s, 1H); $[\alpha]_D^{25}=-99°$ (c=1.0, Chloroform).

General Method of Preparation of Compounds of Formula (1a) and Formula (1b) Via Scheme2

Compounds of Formula 2 in Scheme 2 were prepared as described in WO 2009109983. The racemic compounds of Formula 2 were first analyzed by analytical HPLC on chiral column to get separation and developed the conditions for preparative chiral HPLC in order to isolate the enantiomers in pure form. Thus, the racemic compounds of Formula 2 were separated into their R and S enantiomers of Formula (1a) and Formula (1b) respectively, using chiral preparative HPLC. The analytical as well as chiral preparative HPLC was carried out under following general conditions:

| HPLC column | Chiracel-OD-H (DAICEL) or its equivalent, or Chiracel OJ or its equivalent, or Chiralpak AD or its equivalent |
|---|---|
| Mobile Phase | Alcohol:Hydrocarbon or Alcohol:Hydrocarbon:Alkylamine |
| Wavelength | 254 nm |

Example 6

The racemic compounds of Formula 2 were separated into their R and S enantiomers of Formula (1a) and Formula (1b) respectively using preparative HPLC under following conditions, and the retention time for various compounds are shown in the following table 6:

| HPLC column | Chiralcel-OD-H (250 × 4.6 mm) (DAICEL) |
|---|---|
| Mobile Phase | Ethanol:n-Hexane (15:85) |
| Wavelength | 254 nm |

TABLE 6

Retention times

| Serial No. | Compound No. | Retention Time (RT) min |
|---|---|---|
| 1 | Formula 1a-01 | 18.558 |
|   | Formula 1b-01 | 24.333 |
| 2 | Formula 1a-02 | 19.608 |
|   | Formula 1b-02 | 25.567 |
| 3 | Formula 1a-03 | 17.358 |
|   | Formula 1b-03 | 22.592 |
| 4 | Formula 1a-04 | 22.208 |
|   | Formula 1b-04 | 30.983 |

Example 7

The racemic compounds of Formula 2 were separated into their R and S enantiomers of Formula (1a) and Formula (1b) respectively using preparative HPLC under following conditions and the retention time for various compounds are shown in the following table 7:

| HPLC column | Chiralcel-OD-H (250 × 10 mm) (DAICEL) |
|---|---|
| Mobile Phase | Ethanol:n-Hexane:Diethylamine (20:80:0.1) |
| Wavelength | 254 nm |

TABLE 7

Retention times

| Serial No. | Compound No. | Retention Time (RT) min |
|---|---|---|
| 1 | Formula 1a-01 | 21.68 |
|   | Formula 1b-01 | 29.62 |
| 2 | Formula 1a-02 | 19.98 |
|   | Formula 1b-02 | 30.47 |
| 3 | Formula 1a-03 | 19.79 |
|   | Formula 1b-03 | 30.45 |
| 4 | Formula 1a-04 | 22.23 |
|   | Formula 1b-04 | 33.72 |

Example 8

The racemic compounds of Formula 2 were separated into their R and S enantiomers of Formula (1a) and Formula (1b) respectively using preparative HPLC under following conditions and the retention time for various compounds are shown in the following table 8:

| HPLC column | Chiralpak-AD (250 × 10 mm) (DAICEL) |
|---|---|
| Mobile Phase | Isopropylalcohol:Heptane:Diethylamine (15:85:0.1) |
| Wavelength | 254 nm |

TABLE 8

Retention times

| Serial No. | Compound No. | Retention Time (RT) min |
|---|---|---|
| 1 | Formula 1a-01 | 20.23 |
|   | Formula 1b-01 | 32.43 |
| 2 | Formula 1a-02 | 21.10 |
|   | Formula 1b-02 | 32.17 |
| 3 | Formula 1a-03 | 20.52 |
|   | Formula 1b-03 | 31.42 |
| 4 | Formula 1a-04 | 23.56 |
|   | Formula 1b-04 | 34.14 |

After carrying out the chiral preparative HPLC, the resulting products were analysed by chiral analytical HPLC for ascertaining optical purity. The optical rotations for various compounds are shown in the following table 9.

TABLE 9

Optical rotations

| Serial No. | Compound No. | Specific Rotation $[\alpha]_D^{24} = \dfrac{\text{Obs. Rotation} \times 100}{\text{Conc.} \times \text{Length}}$ |
|---|---|---|
| 1 | Formula 1a-01 | −97° (C = 1.0, Chloroform) |
|   | Formula 1b-01 | +96° (C = 1.0, Chloroform) |

TABLE 9-continued

| | | Optical rotations | |
|---|---|---|---|
| Serial No. | Compound No. | $[\alpha]_D^{24} = \frac{\text{Obs. Rotation} \times 100}{\text{Conc.} \times \text{Length}}$ | |
| | | Specific Rotation | |
| 2 | Formula 1a-02 | −99° (C = 1.0, Chloroform) | |
| | Formula 1b-02 | +98° (C = 1.0, Chloroform) | |
| 3 | Formula 1a-03 | −111° (C = 1.0, Chloroform) | |
| | Formula 1b-03 | +110° (C = 1.0, Chloroform) | |
| 4 | Formula 1a-04 | −93° (C = 1.0, Chloroform) | |
| | Formula 1b-04 | +92° (C = 1.0, Chloroform) | |

Antifungal Activity Testing:

The compounds of Formula (1a) and (1b) were tested for antifungal activity against various strains of *Candida* (CA 01: *Candida albicans* ATCC 24433, CA 02: *C. albicans* ATCC 10231, CA 03: *C. albicans* ATCC 2091, CA 04: *C. albicans* ATCC 90028, CG 01: *C. glabrata* ATCC 90030, CK 01: *C. Krusei* ATCC 6258, CT 01: *C. tropicalis* ATCC 750). In vitro evaluation of antifungal activity was performed by determining the minimum inhibitory concentration (MIC) following standard broth dilution methods (CLSI: Reference method for broth dilution antifungal susceptibility testing of yeasts; Approved standard, second edition M27-A2, 2002; CLSI: Reference method for broth dilution antifungal susceptibility testing of filamentous fungi; Approved standard M38-A, 2002) with RPMI 1640 medium buffered to pH 7.0 with MOPS buffer. Known anti-fungal agents like Fluconazole and Amphotericin-B were used as standards. End points were determined after 48 hours visually and by using spectrophotometer wherever necessary. The activity parameters are enumerated in Table 10:

TABLE 10

| | $MIC_{50}$ obtained by broth dilution method | | | | | | | | | | |
|---|---|---|---|---|---|---|---|---|---|---|---|
| | MIC in µg/ml | | | | | | | | | | |
| Fungus | AMB | FLU | 2-02 | 1a-02 | 1b-02 | 2-01 | 1b-01 | 2-03 | 1b-03 | 2-04 | 1b-04 |
| CA01 | 0.25 | 1 | 0.06 | 4 | 0.03 | 0.12 | 0.06 | 0.25 | 0.12 | 0.06 | 0.03 |
| CA02 | 0.5 | 1 | 0.12 | 8 | 0.12 | 0.25 | 0.12 | 0.5 | 0.5 | 0.12 | 0.06 |
| CA03 | 0.5 | 0.5 | 0.25 | 8 | 0.12 | 0.5 | 0.25 | 0.5 | 0.5 | 0.06 | 0.03 |
| CA04 | 0.5 | 0.5 | 0.06 | 4 | 0.03 | 0.25 | 0.12 | 0.5 | 0.25 | 0.06 | 0.03 |
| CG01 | 0.25 | 4 | 0.12 | 4 | 0.06 | 0.25 | 0.12 | 0.5 | 0.25 | 0.06 | 0.03 |
| CK01 | 0.5 | 64 | 1 | >16 | 1 | 1 | 1 | 2 | 1 | 2 | 1 |
| CT01 | 0.5 | 2 | 0.12 | 16 | 0.06 | 0.5 | 0.25 | 2 | 1 | 0.12 | 0.06 |

*For azoles and NCEs: For Fluconazole and the NCEs, MIC is recorded as the concentration exhibiting more than 50% inhibition as compared to the positive control.
For Amphotericin B: MIC is recorded as the concentration exhibiting complete inhibition.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive.

We claim:

1. An optically active antifungal compound of Formula (1b) or a pharmaceutically acceptable salt thereof,

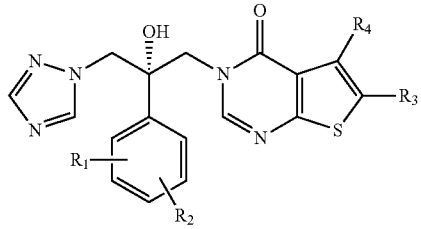

wherein:
said antifungal compound of Formula (1b) is the (S)-enantiomer;
$R_1$ is hydrogen, fluorine, chlorine, bromine or iodine;
$R_2$ is hydrogen, fluorine, chlorine, bromine or iodine; and either
a) $R_3$ and $R_4$ are independently selected from the group consisting of hydrogen or a linear or branched alkyl group having from 1 to 20 carbon atoms, said linear or branched alkyl group optionally substituted with an aryl group, a hydroxyl group, an alkanoate group, an acetoxy group, an amino acetoxy group, a N-Boc-amino acetoxy group, an alkoxy group having from 1 to 4 carbon atoms, a benzyloxy, and an arylalkyl group; or
b) $R_3$ and $R_4$ together form a cycloalkyl ring having from 3 to 10 carbon atoms.

2. The antifungal compound of Formula (1b) as claimed in claim 1, wherein at least one of $R_3$ and $R_4$ is said linear or branched alkyl group having from 1 to 20 carbon atoms.

3. The antifungal compound of Formula (1b) as claimed in claim 1, wherein said arylalkyl group comprises a phenyl group, said phenyl group being optionally substituted with an alkyl group having 1 to 3 carbon atoms.

4. An optically active antifungal compound of Formula (1a) or a pharmaceutically acceptable salt thereof,

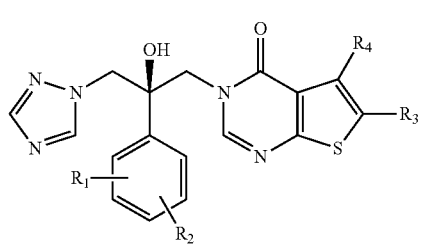

wherein:
said antifungal compound of Formula (1a) is the (R)-enantiomer;
R$_1$ is hydrogen, fluorine, chlorine, bromine or iodine;
R$_2$ is hydrogen, fluorine, chlorine, bromine or iodine; and either
a) R$_3$ and R$_4$ are independently selected from the group consisting of hydrogen or a linear or branched alkyl group having from 1 to 20 carbon atoms, said linear or branched alkyl group optionally substituted with an aryl group, a hydroxyl group, an alkanoate group, an acetoxy group, an amino acetoxy group, a N-Boc-amino acetoxy group, an alkoxy group having from 1 to 4 carbon atoms, a benzyloxy, and an arylalkyl group; or
b) R$_3$ and R$_4$ together form a cycloalkyl ring having from 3 to 10 carbon atoms.

5. The antifungal compound of Formula (1a) as claimed in claim 4, wherein said arylalkyl group comprises a phenyl group, said phenyl group being optionally substituted with an alkyl group having 1 to 3 carbon atoms.

6. A pharmaceutical composition for treating fungal infections, comprising a compound of Formula (1b) according to claim 1, in association with at least one pharmaceutical excipient.

7. A process for preparation of the antifungal compound of Formula (1b) as claimed in claim 1, comprising a reaction of a compound of Formula (3) with a chiral epoxide of Formula (4b), in presence of a base and a catalyst:

Formula (3)

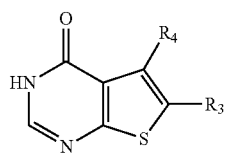

Formula (4b)

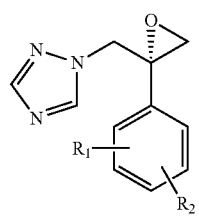

wherein R$_1$, R$_2$, R$_3$ and R$_4$ are as defined in claim 1.

8. A process for preparation of the antifungal compound of Formula (1a) as claimed in claim 4, comprising a reaction of a compound of Formula (3) with a chiral epoxide of Formula (4a), in presence of a base and a catalyst:

Formula (3)

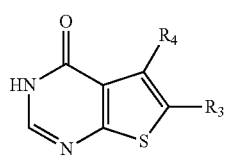

Formula (4a)

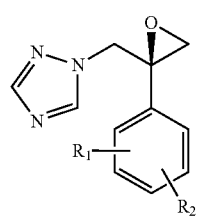

wherein R$_1$, R$_2$, R$_3$ and R$_4$ are as defined in claim 4.

9. The process as claimed in claim 7, wherein the base is selected from the group consisting of organic and inorganic bases.

10. The process as claimed in claim 7, wherein the base is selected from the group consisting of potassium carbonate, sodium carbonate and cesium carbonate.

11. The process as claimed in claim 8, wherein the base is selected from the group consisting of organic and inorganic bases.

12. The process as claimed in claim 8, wherein the base is selected from the group consisting of potassium carbonate, sodium carbonate and cesium carbonate.

13. The process as claimed in claim 7, wherein the catalyst is selected from the group consisting of tetrabutylammonium bromide, tetrabutylammonium chloride, triethylbenzylammonium chloride or cetyltrimethylammonium bromide, and mixtures thereof.

14. The process as claimed in claim 8, wherein the catalyst is selected from the group consisting of tetrabutylammonium bromide, tetrabutylammonium chloride, triethylbenzylammonium chloride, cetyltrimethylammonium bromide, and mixtures thereof.

15. A process for preparation of the antifungal compound of Formula (1b) according to claim 1, said process comprising chiral separation of a mixture of the compound of Formula (1b) and a compound of Formula (1a) using HPLC, 1a

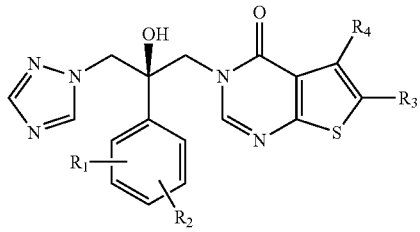

wherein:
HPLC is carried out on a chiral preparative HPLC column comprising:
cellulose tris (3,5-dimethylphenylcarbamate) coated on silica-gel,
cellulose tris (4-methylbenzoate) coated on silica-gel, or
tris-(3,5-dimethylphenyl)-carbamoyl amylose coated on silica-gel; and
HPLC is carried out using an eluent system, said eluent system being an isocratic system comprising a mixture of at least one hydrocarbon, at least one alcohol, and optionally at least one alkylamine.

16. The process as claimed in claim 15, wherein the hydrocarbon is selected from the group consisting of pentane, hexane, heptane, iso-octane, cyclohexane, cyclopentane, and mixtures thereof.

17. The process as claimed in claim 15, wherein the alcohol is selected from the group consisting of methanol, ethanol, propan-1-ol, propan-2-ol, butan-1-ol, butan-2-ol, tert-butanol, 3-methyl-1-butanol, 2-methyl-1-propanol, 2-methoxyethanol, 2-ethoxyethanol, and mixtures thereof.

18. The process as claimed in claim 15, wherein the eluent comprises from 0% to 2% of an alkylamine, said alkylamine being selected from the group consisting of diethylamine, triethylamine, isopropylamine, butylamine, and mixtures thereof.

19. A process for preparation of the antifungal compound of Formula (1a) according to claim 4, said process comprising chiral separation of a mixture of the compound of Formula (1a) and a compound of Formula (1b) using HPLC,

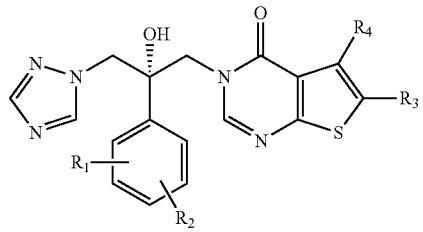

wherein:
  HPLC is carried out on a chiral preparative HPLC column comprising:
    cellulose tris (3,5-dimethylphenylcarbamate) coated on silica-gel,
    cellulose tris (4-methylbenzoate) coated on silica-gel, or
    tris-(3,5-dimethylphenyl)-carbamoyl amylose coated on silica-gel; and
  HPLC is carried out using an eluent system, said eluent system being an isocratic system comprising a mixture of at least one hydrocarbon, at least one alcohol, and optionally at least one alkylamine.

20. A method for treating a fungal infection in a subject in need thereof, which method comprises administering an effective amount of the compound of Formula (1b) according to claim 1 to said subject.

* * * * *